United States Patent [19]
Roberts

[11] Patent Number: 5,590,774
[45] Date of Patent: Jan. 7, 1997

[54] SURGICAL NEEDLE DISCARD CONTAINER

[76] Inventor: Holly H. Roberts, 365 Broad St., Red Bank, N.J. 07701

[21] Appl. No.: 466,783

[22] Filed: Jun. 6, 1995

[51] Int. Cl.$^6$ .................................................. B65D 83/10
[52] U.S. Cl. .......................... 206/366; 206/370; 206/380; 220/254
[58] Field of Search ................................. 206/366, 370, 206/380, 540, 533, 539; 220/254; 225/1, 89, 43; 221/93, 94, 303, 306

[56] References Cited

U.S. PATENT DOCUMENTS

| | | |
|---|---|---|
| 100,879 | 3/1870 | Field . |
| D. 263,505 | 3/1982 | Black . |
| 437,543 | 9/1890 | Wilburn . |
| 1,817,562 | 8/1931 | Hodge . |
| 2,903,127 | 9/1959 | Dorman . |
| 3,292,776 | 12/1966 | Penn . |
| 3,720,346 | 3/1973 | Cypher .................................. 220/254 |
| 4,165,709 | 8/1979 | Studer . |
| 4,203,518 | 5/1980 | Current . |
| 4,586,614 | 5/1986 | Ger . |
| 4,657,139 | 4/1987 | Hanifl . |
| 4,813,173 | 3/1989 | Abbotoy . |
| 4,867,309 | 9/1989 | Germain ................................. 206/366 |
| 4,991,737 | 2/1991 | Edelman ................................ 220/254 |
| 5,150,788 | 9/1992 | Weissman ............................... 206/370 |

*Primary Examiner*—David T. Fidei
*Attorney, Agent, or Firm*—McAulay Fisher Nissen Goldberg & Kiel, LLP

[57] ABSTRACT

A surgical needle discard container which includes a plurality of needle receiving compartments defined therein. A lid is rotatably attached to one end of the container to block access to compartments not in use. An aperture defined in the lid provides access to one of the compartments. The aperture is selectively aligned with each compartment as the lid is rotated relative to the container by an advancing mechanism. A cutting device associated with the lid and container severs the portion of a suture that extends beyond the end of the container from a needle disposed in one of the compartments by rotating the lid relative to the container.

20 Claims, 3 Drawing Sheets

5,590,774

SURGICAL NEEDLE DISCARD CONTAINER

BACKGROUND OF THE INVENTION

1. Field of the Invention

The present invention relates to a device for safely storing used surgical needles, and, in particular, to a multicompartment discard container, wherein each used surgical needle is placed in a separate compartment within the container, thereby permitting the used needles to be easily counted while being safely contained and discarded.

2. Description of the Related Art

Surgical needles, which are used to insert a suture during surgery, represent a serious danger to a patient if not removed from the surgical cite. For example, if a needle is left in the patient, it may perforate vital organs, cause infection, and even result in death. Therefore, it is imperative that all surgical needles are counted at the beginning of a surgical procedure and at the end of the procedure.

Typically, the used needles are recounted several times to ensure that each needle is accounted for, i.e., that none of the needles are left in the patient. Because the used needles are repeatedly counted, the used needles should be stored in a device that permits recounting.

A used surgical needle also represents a danger to the medical personnel responsible for handling the needles. If a used needle perforates the attendant's skin, that needle could transmit some infectious diseases from the patient to the attendant by blood-to-blood contact. Avoiding this problem requires storing the used needles in a device that minimizes the chances of the used needle contacting an individual. This is made difficult by the fact that used surgical needles should remain visible so that an accurate count of the needles can be made repeatedly.

One conventional needle counting device that attempts to achieve these objectives consists of a flat, bar-shaped magnetic pad having a plurality of sections identified thereon. After each needle is used, the surgical assistant places the used needle on top of the successively numbered portions of the magnetic pad so that an accurate count of the used needles can be made at the end of the surgical procedure. This conventional counting device, however, does not adequately prevent individuals from being exposed to the used needles because the needles remain unshielded when placed on the surface of the magnetic pad. The ends of many needles extend beyond the magnetic pad. The risk of exposure to the used needles is especially great when the needles are ultimately disposed of.

In addition, because the used needles typically include a portion of a suture attached thereto, the collection of needles and sutures on an open pad can make this needle discarding system cumbersome, and the indicia on the magnetic pad may be obscured thereby preventing the number of used needles stored thereon from being quickly counted. In addition, the sutures attached to the needles placed on the magnetic pad can get snagged, pulled, etc., thereby displacing the used needles from their proper position on the magnetic pad. To avoid these problems, a separate cutting device, such as a pair of scissors, must be available for cutting the excessive lengths of suture from the used needles so that the used needles can be effectively stored on the magnetic pad.

Another conventional discard device consists of a box with a sponge or solid foam material provided at the bottom thereof. A plurality of sections are identified on the sponge material so that the tip of the used needles can be inserted into successive sections of the sponge. This configuration permits an accurate count to be made of the used needles. However, because all the used needles are inserted into a sponge that is contained within the same box, this discard device also does not adequately prevent the surgical assistant from being exposed to injury from the used needles because the box is not closed until the end of the operative procedure.

Furthermore, the lengths of suture attached to the used needles can make accurately inserting the used needles into their proper location even more difficult and dangerous, especially in an operating room environment where situations may arise that require surgical assistants to perform such tasks quite rapidly. In addition, the suture attached to the needles can be inadvertently pulled causing the needles to be pulled out of the sponge or can interfere with the closing of the box. To cut the suture, a pair of scissors is used.

In an invasive surgical procedure, a substantial amount of blood is present on the surgeons' and nurses' glove covered hands. Anything that these personnel handle is covered with blood. Some procedures become stressful when unforeseen circumstances arise. Small objects like needles can easily become lost in the profuse field of blood. So a device like a needle container should be easy to handle yet safe, easy to operate yet provide a ready visual verification of the number of needles contained therein.

SUMMARY OF THE INVENTION

It is an object of the present invention to provide a discard container for used surgical needles that overcomes the problems associated with previously known surgical needle storage devices.

It is a further object of the present invention to provide a discard container that both 1) stores used surgical needles in a manner that minimizes the risk of attendants being stuck by a needle and 2) facilitates quick, easy, and reliable counting of the used needles.

It is a still further object of the present invention to provide a discard container that does not require a separate, supplemental cutting device, such as a pair of scissors, for removing excess lengths of suture from the used needle.

In accordance with the principles of the present invention, the foregoing objects are achieved by providing a surgical needle discard container that stores used surgical needles therein. The discard container includes a container having a plurality of separate compartments defined therein. Each compartment is sized so as to receive a surgical needle therein. A lid is rotatably attached to one end of the container. The lid has an aperture defined therein for providing selective access to one of the plurality of compartments while blocking access to the rest of the compartments. The aperture is individually aligned with each compartment as the lid is rotated relative to the container. A ratchet mechanism is provided with respect to the container and lid to permit incremental rotation of the lid relative to the container in only one direction so that the aperture is selectively aligned with each compartment. In addition, the discard container includes a cutting device associated with the container and the lid. The cutting device severs the portion of the suture that extends out of the end of the container from the needle disposed in one of the compartments when the lid is rotated relative to the container.

As will become apparent from the detailed description below, the present invention solves the above-identified problems with conventional surgical needle discard devices by sealing each used surgical needle in its own compartment so that they are not a source of danger to the medical personnel. By rotating the lid, no more than substantially one full turn, each needle is captured in its own individual compartment and the excess length of suture is removed therefrom. At the end of the surgical procedure, the needles can be quickly, accurately, and safely counted by visualizing each needle in its own compartment. The compartments may be numbered to facilitate counting. The entire discard container can then be discarded.

Other objects, features and characteristics of the present invention as well as the methods of operation and function of the related elements of structure, and the combination of parts and economies of manufacture, will become more apparent upon consideration of the following detailed description and the appended claims with reference to the accompanying drawings, all of which form a part of this specification, wherein like reference numerals designate corresponding parts in the various figures.

DETAILED DESCRIPTION OF THE PRESENTLY PREFERRED EXEMPLARY EMBODIMENTS

Figure 1:
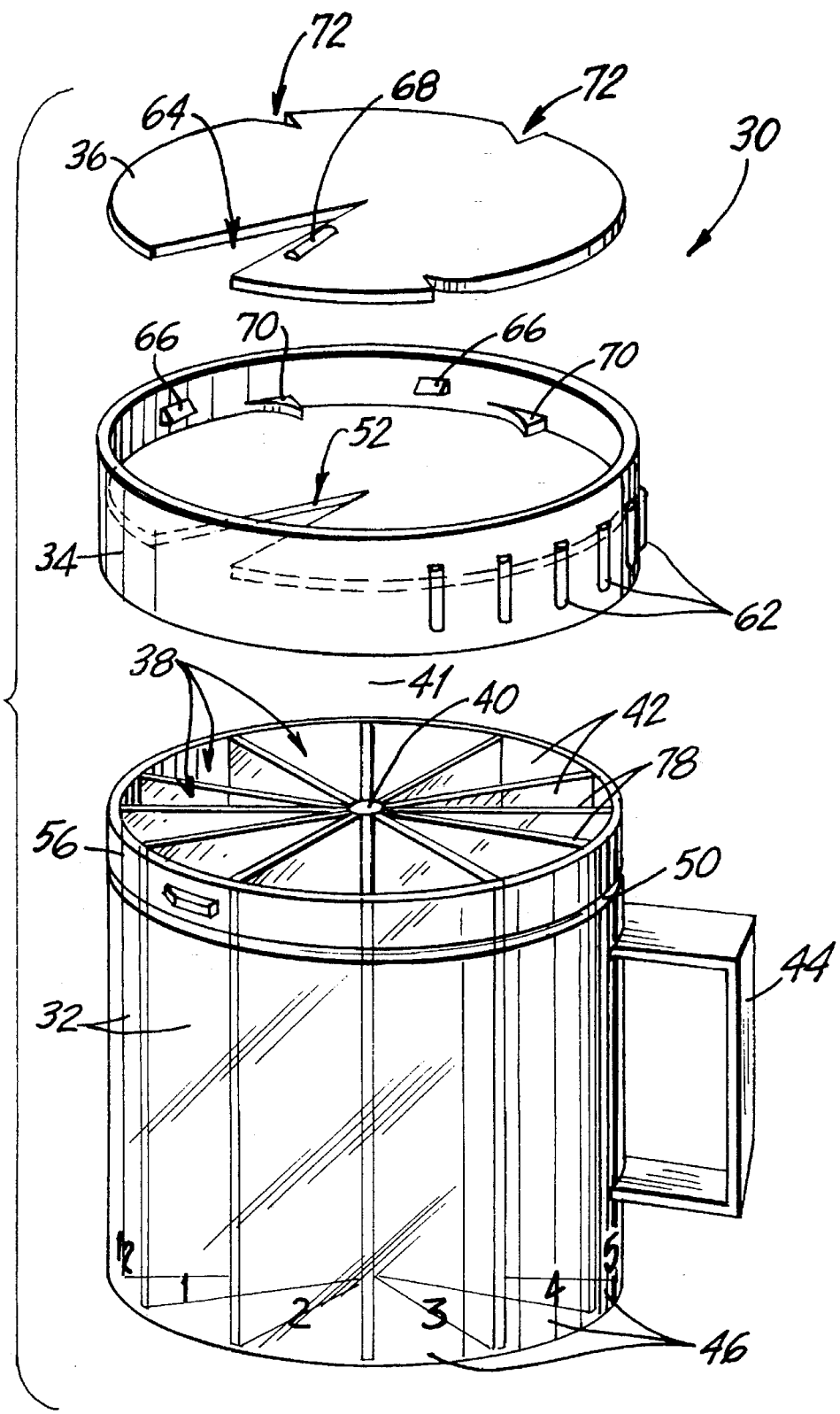
FIG. 1 is an exploded perspective view of a first embodiment of the used needle storage device of the present invention.
Figure 2:
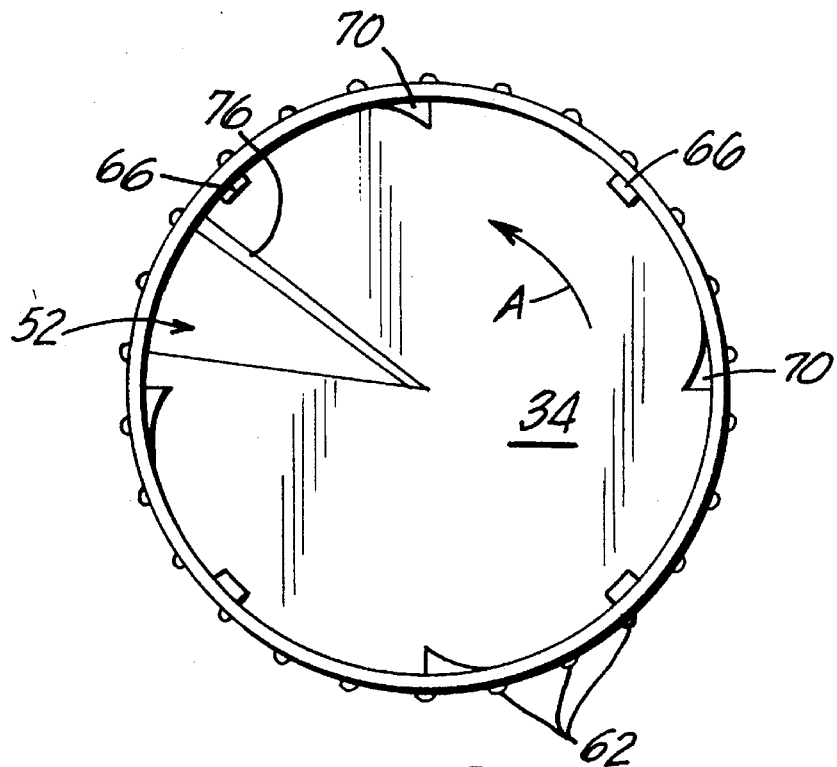
FIG. 2 is a top view of the lid of the needle discard container illustrated in FIG. 1.
Figure 6:
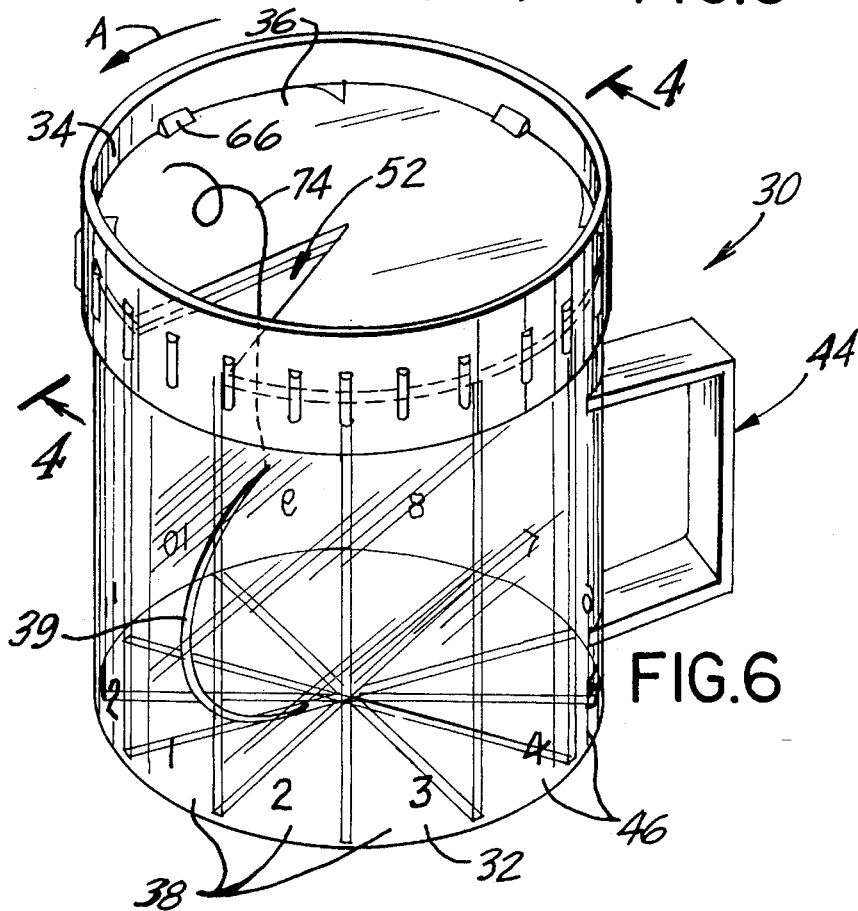
FIG. 6 is a perspective view of the assembled needle discard container.

FIGS. 1 and 6 illustrate a surgical needle discard container, generally indicated at 30, according to the principles of the present invention. Discard container 30 includes a container 32, a lid 34, a lid cover 36, and a handle 44. Container 32 is generally cylindrical and divided into a plurality of circumferentially arranged, wedge-shaped, compartments 38 around a central hub 40. Central hub 40 is aligned with a longitudinal axis 41 of container 32. A plurality of spoke-like dividers 42 radiate from central hub 40 to an outer wall of cylindrical container 32 to define compartments 38. Dividers 42 extend the full height of cylindrical container 32 so as to isolate each compartment 38 from an adjacent compartment. The dividing walls 42 should be made of a material that enhances counting and visualization of needles. In the illustrated embodiment, compartments 38 are sized so as to easily accommodate a surgical needle 39 having a variety of different shapes and sizes therein.

Container 32 can be made from a variety of materials. However, in the illustrated embodiment, container 32 is made from a material that permits visualization of the contents of each compartment 38 so that one can quickly verify that a needle has been placed in a compartment. An example of a suitable material is clear plastic.

A plurality of indicia 46 are provided around the perimeter of container 32 to identify each compartment 38. In an exemplary embodiment of the present invention, indicia 46 are integral with the container, defined during molding, for economies of manufacture. Permitting visual inspection of the needles discarded in each compartment of container 32 and providing indicia 46 enable the number of needles used during an operation to be easily counted and recounted without exposing the user to the needles.

Lid 34 is rotatably attached to container 32. Details of lid 34 are shown in FIGS. 2, 3, 4, and 5. In the illustrated embodiment, lid 34 includes an inwardly extending circumferential lip 48 around a lower portion thereof. Lip 48 engages a circumferentially concave groove 50 provided around the perimeter of container 32 so that lid 34 snaps onto container 32 and can be rotated relative thereto. Lip 48 and groove 50 are sized and shaped so that once lid 34 is attached to container 32, lid 34 cannot be easily removed therefrom. It is to be understood, however, that lid 34 can be attached to container 32 in a variety of different ways so long as lid 34 is rotatable relative to container 32. By attaching lid 34 in the manner illustrated, however, lid 34 can be removed from container 32 and replaced thereon without damaging either lid 34 or container 32, should the need arise.

Lid 34 includes an aperture 52 defined therein. Aperture 52 is sized and shaped so as to substantially correspond to the shape of the compartment 38 when viewed from the top of the container. Lid 34 is positioned on the end of container 32 such that aperture 52 aligns with one of the compartments 38 thereby providing access to that compartment while access to the other compartments is blocked by the remaining portions of lid 34. As lid 34 rotates in a direction, such as that indicated by arrow A, aperture 52 is sequentially aligned with each individual compartment 38. A used surgical needle is then placed in the compartment to which access is provided. Lid 34 is then further rotated relative to container 32 to provide access to the next adjacent compartment while blocking access to the preceding compartment in which the used needle is now located. Thus, the used needles are safely, individually stored in separate compartments in discard container 30. Thereafter, the entire discard container, including the surgical needles disposed therein, can be easily and safely disposed of without exposing the user to the used needles.

Discard container 30 includes a mechanism that permits incremental rotation of lid 34 relative to container 32 so that aperture 52 is maintained in an aligned relationship with one of the compartments at a time. Each incremental rotation of lid 34 places lid 34 into an aligned relationship with the next subsequent compartment. This mechanism also permits lid 34 to be rotated relative to container 32 in only one direction so that once a needle has been placed in a compartment, lid 34 can not be rotated backward, thereby locking needle 39 within a compartment.

In the illustrated embodiment this mechanism is a ratchet. The ratchet includes a plurality of ratchet teeth 54 circumferentially provided on an inside surface of lid 34. Each tooth 54 is essentially an elongated, raised protuberance on the surface of lid 34 and includes an inclined leading edge. At least one ratchet tooth 56 is also provided on the outer surface of container 32. The ratchet teeth 54 on the inside lid 34 are oriented to engage and pass over ratchet tooth 56 shown in FIG. 1 when lid 34 is properly positioned on container 32. Ratchet teeth 54 are sized and spaced relative to one another so that tooth 56 is firmly held between two adjacent ratchet teeth 54.

When lid 34 is rotated relative to container 32, the inclined surfaces of ratchet teeth 54 and 56 engage and produce a slight lifting effect whereby as one of the teeth 54 pass over ratchet tooth 56 so that ratchet tooth 56 is again adjacent to the next ratchet teeth 54. This arrangement of ratchet teeth 54 and 56 allows incremental rotation of lid 34 relative to container 32, assists in aligning aperture 52 over each compartment 38, and locks lid 34 in position until the next incremental rotation is required. The ratchet teeth size and spacing therebetween are selected so that aperture 52 is individually registered with each compartment during the rotation of lid 34 relative to container 32.

It is to be understood that the ratchet mechanism illustrated in the drawings is provided for purposes of illustration and may not be to scale. It is to be further understood that other sizes, shapes, and orientations, of the ratchet teeth are contemplated by the present invention. For example, while the ratchet mechanism has been illustrated with a plurality of teeth provided on lid 34 and a single tooth provided on container 32, this arrangement can be reversed.

Figure 3:
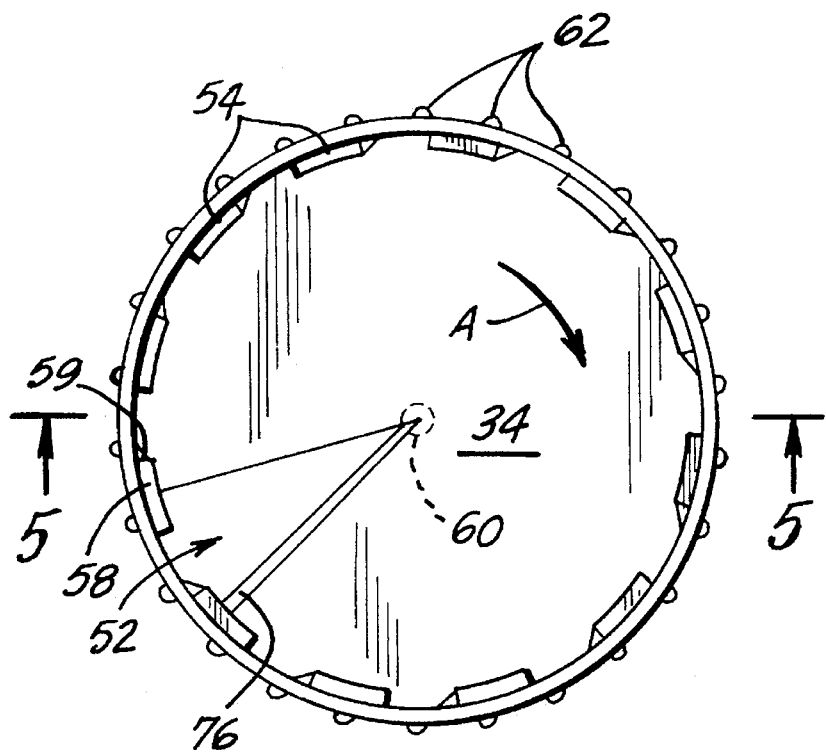
FIG. 3 is a bottom view of the lid used in the needle discard container illustrated in FIG. 1.
Figure 4:
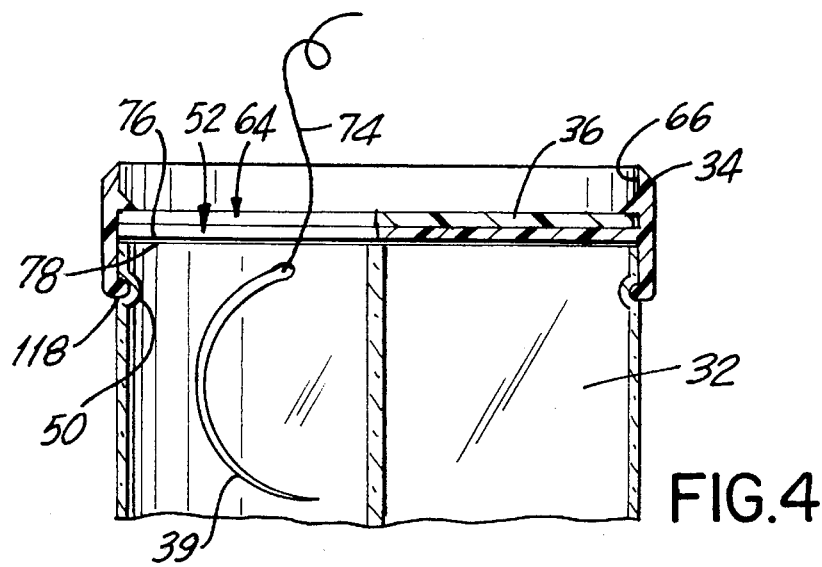
FIG. 4 is a partial cross-sectional view of the needle discard container illustrated in FIG. 6 taken along line 4—4.
Figure 5:
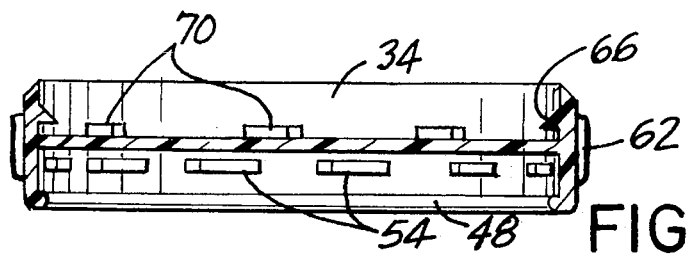
FIG. 5 is a cross-sectional view of the lid illustrated in FIG. 3 taken along line 5—5.

The ratchet mechanism of the present invention includes a stopping member 58 shown in FIG. 3 that prevents lid 34 from being rotated greater than one full turn. This prevents additional used needles from being inserted into occupied compartments once each compartment has been filled. In the illustrated embodiment, stopping member 58 is formed by providing the last ratchet tooth from among ratchet teeth 54 with an abrupt leading edge 59. The last ratchet tooth 58 is that tooth, from among ratchet teeth 54, that is the last to engage tooth 56 before engagement between ratchet teeth 54 and tooth 56 could otherwise be repeated. In FIG. 3, stopping member 58 is at the leading edge of lid aperture 52. Prior to rotation of lid 34, stopping member 58 is aligned between the first and second compartments when lid 34 is attached to container 32 and aperture 52 is aligned with the first compartment. As lid 34 rotates counterclockwise relative to container 32, aperture 52 aligns with each compartment. When aperture 52 aligns with the last compartment, stopping member 58 is adjacent tooth 56, which is positioned proximate to the first compartment. The flat leading edge 59 of the stopping member 58 significantly impedes stopping member 58 from overriding ratchet tooth 56 on container 32 so that aperture 52 cannot be easily rotated from registration with the last compartment to the initial (first) compartment.

It is to be understood that other mechanisms for preventing greater that one full rotation of lid 34 are contemplated by the present invention. For example, lid 34 and/or container 32 can include a protruding member or protruding members that engage one another after one complete rotation of lid 34, thereby preventing additional rotation.

Although not illustrated in the present figures, hub 40 can be elevated and lid 34 provided with a recess 60 (FIG. 3) to receive the elevated hub therein when lid 34 is attached to container 32. This arrangement between the elevated hub and the recess in lid 34 acts as a stabilizer to prevent excess lateral movement between lid 34 and container 32. This arrangement provides accurate concentric alignment between rotating lid 34 and the elevated hub so that accurate alignment of compartments 38 in container 32 with aperture 52 in lid 34 can be achieved.

In the illustrated embodiment, lid 34 includes thumb grips 62 provided on an outer peripheral surface thereof. Thumb grips 62 facilitate manual rotation of lid 34 relative to container 32 by providing grips which an attendant's thumb can push against to advance lid 34. Providing thumb grips 62 and handle 44 permit the surgical assistant to hold discard container 30 and rotate lid 34 relative to container 32 at the same time using the same hand by inserting the fingers in handle 44 and using the thumb to rotate lid 34. While thumb grips 62 have been illustrated and described in conjunction with lid 34, it is to be understood that a variety of different configurations for the outer peripheral surface of lid 34 are possible to facilitate rotation. Knurling the outer peripheral surface of lid 34 is an example of such an alternative configuration.

Lid cover 36 is provided for selectively blocking aperture 52 in lid 34. In the illustrated embodiment, lid cover 36 comprises a substantially flat disc having a lid cover aperture 64 defined therein. Lid cover aperture 64, like aperture 52, has a size and shape that substantially matches the size and shape compartment 38 when viewed from the top of the container. In the illustrated embodiment, lid cover 36 is rotatably attached to lid 34 and lid cover aperture 64 is aligned directly over aperture 52 to permit the used needles to pass through both apertures 64 and 52 into compartments 38. Lid cover 36 selectively closes aperture 52 by rotating lid cover 36 relative to lid 34 such that a portion of lid cover 36 overlies aperture 52.

Lid cover 36 is held in close proximity to lid 34 by protrusions 66 circumferentially provided on an inside surface of lid 34. Lid cover 36 is sized and shaped so as to be capable of being snapped into position within lid 34 so that protrusions 66 engage a peripheral portion of lid cover 36. The lid cover, once snapped below protrusions 66, cannot be removed as protrusions 66 have a flat lower surface on a bottom portion thereof. The flat lower surfaces of protrusions 66 spaced far enough away from the top flat surface of lid 34 permit lid cover 36 to rotate relative to lid 34. To facilitate its rotation, lid cover 36 includes an elevated handle 68 on a top surface thereof.

A lid cover ratchet mechanism permits incremental clockwise rotation of lid cover 36 relative to lid 34 so that lid cover 36 is maintained in position relative to lid 34 as lid 34 rotates relative to container 32. In addition, once lid cover 36 is rotated, the ratchet mechanism prevents it from rotating counterclockwise.

In the illustrated embodiment, the lid cover ratchet mechanism comprises a plurality of teeth 70 circumferentially provided on an insider surface of lid 34. Teeth 70 engage slots 72 circumferentially provided on the outer periphery of lid cover 36. Teeth 70, like teeth 54, have a slanted leading surface.

While lid cover 36 has been described above with respect to the device illustrated in the figures, it is to be understood that the lid cover can have a variety of different configurations so long at it serves to selectively close aperture 52. For example, lid cover 36 can be rotatable in either a clockwise or counter-clockwise direction. In addition, lid cover 36 need not be rotatably attached to lid 34, but instead, can be a cap that is provided over lid 34 following the completion of the surgical procedure. It is to be understood that other configurations for teeth 70 and slots 72 are possible.

A used surgical needle typically includes a suture 74 still attached thereto. See FIGS. 4 and 6. As a result, when needle 39 is dropped in compartment 38 of container 32, a portion of suture 74 can extend beyond the end of container 32. The excess portion of suture 74 can interfere with the proper operation of discard container 30 and may get snagged. Thus, the present invention includes a cutting device associated with container 32 and lid 34. The cutting device severs the portion of the suture that extends out of the container from the needle in the compartment by rotating the lid relative to the container. In the illustrated embodiment, the cutting device comprises a first cutting blade 76 provided along an edge of the lid defining aperture 52. A second cutting blade 78 or counter blade, opposing the first cutting blade is provided along an edge of each divider 42. Rotating lid 34 relative to container 32 causes first cutting blade 76 to move toward second cutting blade 78 in a scissor-like fashion so as to cut the portion of suture 74 that extends beyond the end of container 32 away from needle 39 disposed in compartment 38. This cutting operation is automatically performed each time the lid is rotated so that additional cutting devices are not required.

It is to be understood that only one cutting blade need be employed in the present invention. If only one cutting blade is used, for example on the edge of the lid defining aperture 52, the other surface on the divider prevents the suture from moving so that the cutting blade can sever the suture from the needle.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

What is claimed is:

1. A surgical needle discard container for storing used surgical needles, comprising:
   a container having a plurality of separate compartments defined therein, each compartment being sized so as to receive a surgical needle therein;
   a lid rotatably attached to one end of said container, said lid having an aperture defined therein, said aperture being selectively aligned with each of said compartments as said lid is rotated relative to said container; and
   a mechanism associated with said container and said lid, said mechanism permitting incremental rotation of said lid relative to said container in only one direction to selectively align said aperture with said compartments.

2. A surgical needle discard container as defined in claim 1, further comprising:
   a cutting device, associated with said container and said lid, said cutting device severing a portion of a suture that extends beyond said end of said container from a needle disposed in one of said compartments when said lid is rotated relative to said container.

3. A surgical needle discard container as defined in claim 2, wherein said cutting device includes a first cutting surface provided along an edge of said lid defining said aperture and a counter blade defined by an edge of a divider that separates said compartments from one another.

4. A surgical needle storing device as defined in claim 1, wherein said mechanism includes a first plurality of teeth disposed on one of an inner peripheral surface of said lid and an outer peripheral surface of said container, and at least one tooth disposed on the other of said inner peripheral surface of said lid and said outer peripheral surface of said container, said first plurality of teeth being arranged in an opposing relation to said at least one tooth so that said first plurality of teeth and said at least one tooth engage each other to allow said incremental rotation of said lid relative to said container in said one direction, and so that said lid aperture is locked into alignment with one of said plurality of compartments.

5. A surgical needle discard container as defined in claim 1, further comprising a stopping member that prevents said lid from rotating more than 360°.

6. A surgical needle discard container as defined in claim 1, wherein said container is cylindrical shaped, wherein said plurality of compartments are disposed in a circular orientation about a longitudinal axis of said container, and wherein each compartment is separated from an adjacent compartment by a divider.

7. A surgical needle discard container as defined in claim 1, wherein at least a portion of said container is made from a material that permits visualization of said needles disposed in each compartment.

8. A surgical needle discard container as defined in claim 1, further comprising indicia identifying each of said compartments in sequential order to facilitate counting of said needles disposed within each compartment.

9. A surgical needle discard container as defined in claim 1, further comprising a lid cover that selectively closes said aperture.

10. A surgical needle discard container as defined in claim 9, wherein said lid cover comprises a substantially flat disc having a lid cover aperture defined therein, said lid cover aperture aligning with said aperture to permit access to one of said plurality of compartments, said lid cover closing said aperture by moving said lid cover relative to said lid so that a portion of said lid cover overlies said aperture.

11. A surgical needle discard container as defined in claim 9, wherein said lid cover is rotatably attached to said lid so as to selectively close said aperture by rotating said lid cover relative to said lid such that a portion of said lid cover overlies said aperture.

12. A surgical needle discard container as defined in claim 11, wherein said lid cover is held in close proximity to said lid by protrusions provided on an inside surface of said lid, said protrusions engaging a peripheral portion of said lid cover.

13. A surgical needle discard container as defined in claim 11, further comprising a lid cover ratchet mechanism that permits incremental rotation of said lid cover relative to said lid so that said lid cover is maintained in position relative to said lid as said lid rotates relative to said container.

14. A surgical needle discard container as defined in claim 1, further comprising at least one handle attached to said container.

15. A surgical needle discard container as defined in claim 14, further comprising protuberances provided on an outer peripheral surface of said lid, said protuberances and said handle being disposed on said lid and said container, respectively, so that a user is capable of both gripping said container and rotating said lid relative to said container using only one hand.

16. A surgical needle discard container as defined in claim 1, further comprising protuberances provided on an outer peripheral surface of said lid to facilitate manual rotation of said lid relative to said compartment.

17. A method for collecting used surgical needles in a device comprising a plurality of compartments, the method characterized by the steps of:
   dropping a needle through an aperture in a lid into a first compartment having at least one transparent wall for visual inspection of the needle;
   rotatably advancing said lid through a predetermined amount to cover said first compartment while simultaneously opening a second compartment; and
   severing a suture that extends through said aperture from the needle that has been dropped into said first compartment simultaneously with said step of covering said first compartment.

18. A device for collecting used surgical needles, the device comprising a plurality of compartments, each having at least one transparent wall, the device characterized by:

first means for permitting a needle to be inserted into a first compartment;

means for rotatably advancing through a predetermined distance said first means, thereby covering said first compartment while opening a second compartment; and means for cutting a suture from the needle simultaneously while said first means is advanced.

19. The device of claim 18 further comprising:

means rotatably advanceable through a predetermined distance for selectivity covering said first means.

20. The device of claim 18 further comprising:

means for preventing said first means from rotating more than one complete turn.

* * * * *